United States Patent [19]

Sakai et al.

[11] Patent Number: 5,131,391
[45] Date of Patent: Jul. 21, 1992

[54] PULSE OXYMETER HAVING PROBE WITH WARMING MEANS

[75] Inventors: Hiroshi Sakai, Kasugai; Satoshi Kohmura, Komaki, both of Japan

[73] Assignee: Colin Electronics Co., Ltd., Aichi, Japan

[21] Appl. No.: 531,099

[22] Filed: May 31, 1990

[30] Foreign Application Priority Data

Jun. 22, 1989 [JP] Japan .................................. 1-160102

[51] Int. Cl.$^5$ .............................................. A61B 5/00
[52] U.S. Cl. .................................................... 128/633
[58] Field of Search ............... 128/633, 637, 664, 666, 128/736, 742; 356/41; 374/142

[56] References Cited

U.S. PATENT DOCUMENTS

| | | |
|---|---|---|
| 4,494,550 | 1/1985 | Blazek et al. |
| 4,860,744 | 8/1989 | Johnson et al. .................. 606/31 |
| 4,880,304 | 11/1989 | Taeb et al. ...................... 128/633 |
| 4,926,867 | 5/1990 | Kanda et al. .................... 128/633 |
| 4,930,506 | 6/1990 | Ullrich ............................ 128/633 |
| 4,972,331 | 11/1990 | Chance ........................... 128/633 |
| 5,007,423 | 4/1991 | Branstetter et al. .............. 128/633 |

FOREIGN PATENT DOCUMENTS 3711272 10/1987 Fed. Rep. of Germany ...... 128/633

Primary Examiner—Stephen C. Pellegrino
Assistant Examiner—Steven J. Shumaker
Attorney, Agent, or Firm—Oliff & Berridge

[57] ABSTRACT

A pulse oxymeter for measuring a blood oxygen saturation of a subject, including a first device for emitting toward a body portion of the subject a first light having a first wavelength and a second light having a second wavelength different from the first wavelength, a second device for detecting an intensity of each of the first and second lights transmitted through, or reflected by, the body portion of the subject and generating a photoelectric pulse wave signal representative of the detected intensity of each of the first and second lights, a third device for determining a blood oxygen saturation of the subject based on the pulse wave signals corresponding to the first and second lights, a probe which supports the first and second devices and is adapted to contact the body portion of the subject, and a warming device for warming the body portion of the subject.

11 Claims, 4 Drawing Sheets

INTENSITY OF REFLECTED LIGHT
(MAGNITUDE OF ELECTRIC SIGNAL SV)

TIME

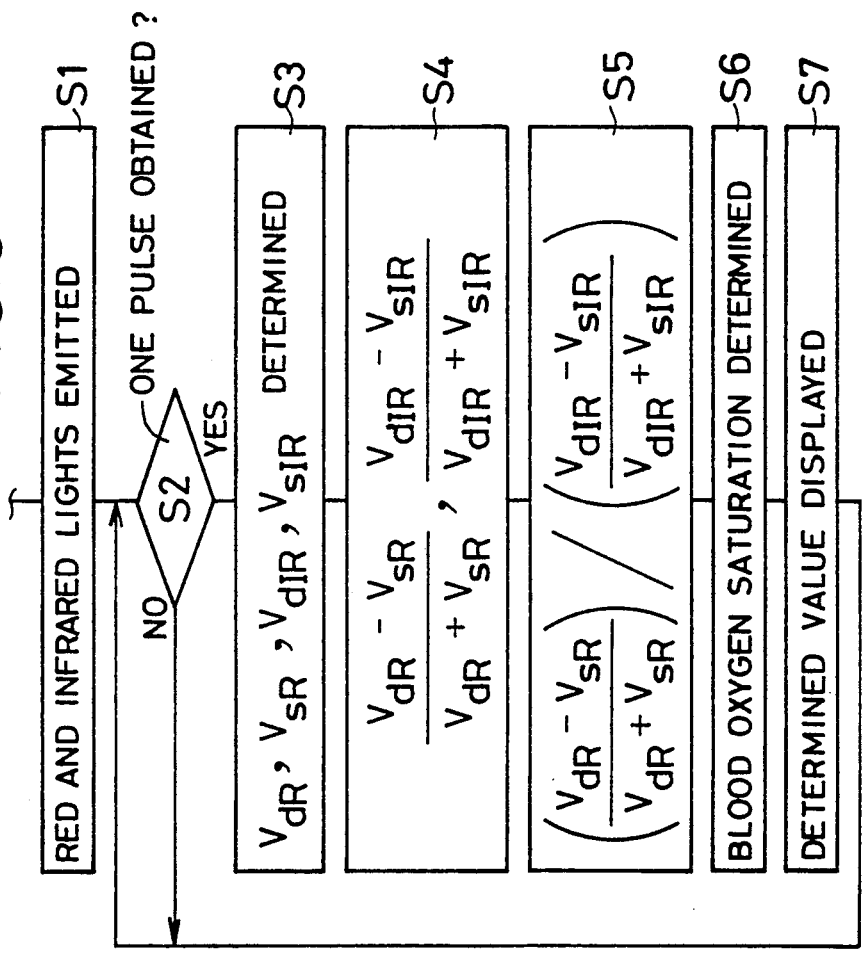

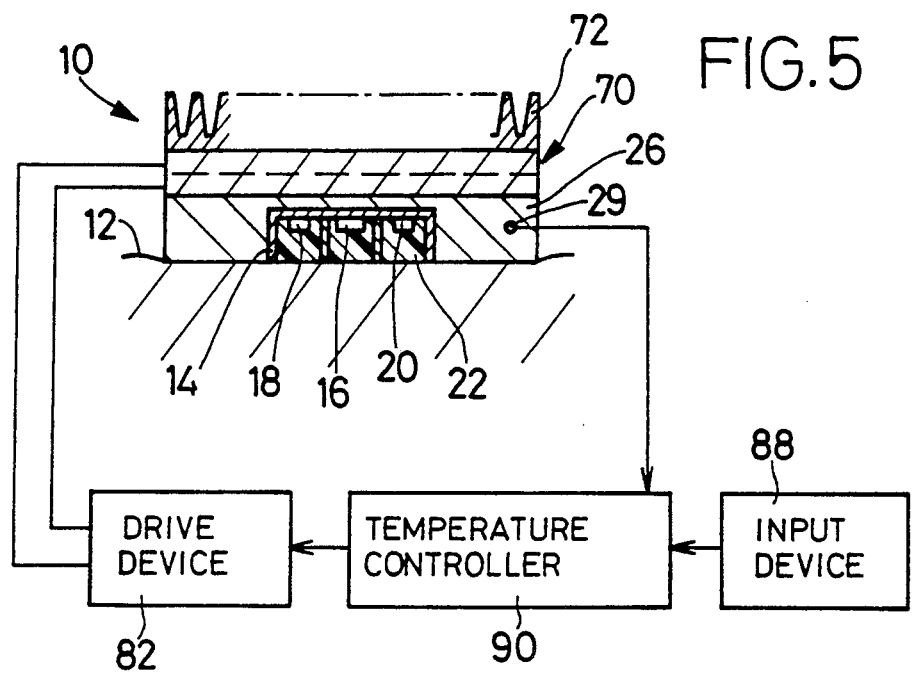
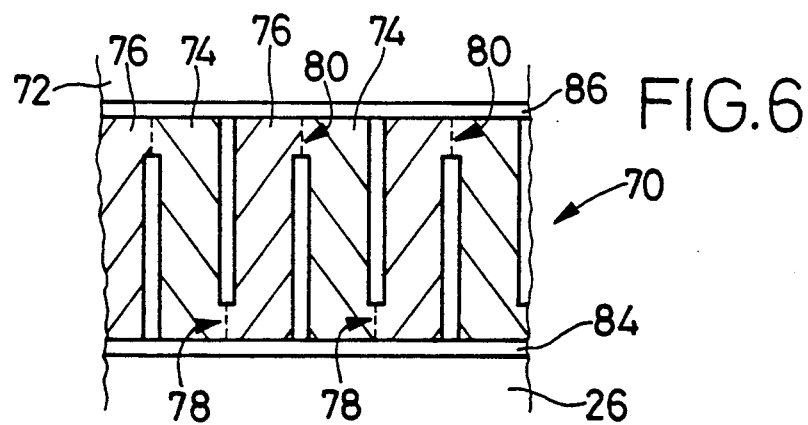

PULSE OXYMETER HAVING PROBE WITH WARMING MEANS

BACKGROUND OF THE INVENTION

1. Field of the Invention

The present invention relates to a pulse oxymeter having a probe which is adapted to be set on a body surface of a subject.

2. Discussion of the Prior Art

There is known a pulse oxymeter for measuring a blood oxygen saturation of a subject, including a probe which supports (a) a first device for emitting toward a body portion of the subject a first light having a first wavelength and a second light having a second wavelength different from the first wavelength, and (b) a second device for detecting an intensity of each of the first and second lights transmitted through, or reflected by, the body portion of the subject and generating a photoelectric pulse wave signal representative of the detected intensity of each of the first and second lights. The pulse oxymeter further includes (c) a third device for determining a blood oxygen saturation of the subject based on the pulse wave signals corresponding to the first and second lights. The probe of the pulse oxymeter is set on a body surface of the subject where a blood oxygen saturation is measured with respect to the blood flowing through the underlying peripheral blood vessels including capillaries.

In the event, however, that a patient is subjected to stress or invasion during a surgical operation, the peripheral blood vessels of the patient may constrict and consequently the blood flow through the peripheral blood vessels may be reduced to an insufficient amount, or lost in an extreme situation. In such events, the pulse oxymeter is not capable of obtaining an appropriate photoelectric pulse wave signal since the amount of the blood flow through the peripheral blood vessels is insufficient, and accordingly the pulse oxymeter is not capable of providing blood oxygen saturation readings in a reliable and precise manner, or carrying out the measurement itself of blood oxygen saturation.

SUMMARY OF THE INVENTION

It is therefore an object of the present invention to provide a pulse oxymeter capable of providing blood oxygen saturation readings in a reliable and precise manner, by preventing constriction of peripheral blood vessels due to invasion, stress, low temperature or the like.

The above object has been achieved by the present invention, which provides a pulse oxymeter for measuring a blood oxygen saturation of a subject, including a first device for emitting toward a body portion of the subject a first light having a first wavelength and a second light having a second wavelength different from the first wavelength, a second device for detecting an intensity of each of the first and second lights transmitted through, or reflected by, the body portion of the subject and generating a photoelectric pulse wave signal representative of the detected intensity of each of the first and second lights, a third device for determining a blood oxygen saturation of the subject based on the pulse wave signals corresponding to the first and second lights, and a probe which supports the first and second devices and is adapted to contact the body portion of the subject, wherein the pulse oxymeter comprises warming means for warming the body portion of the subject.

When the pulse oxymeter constructed as described above is used to measure a blood oxygen saturation of a subject such as a patient, a body portion of the patient on which the probe is set, is warmed by the warming means of the present apparatus. Accordingly, even when the patient is undergoing a surgical invasion during an operation, the warming means serves for preventing constriction of the underlying peripheral blood vessels and thereby ensures that the blood flow through the peripheral blood vessels is maintained at a normal amount. Thus, the present pulse oxymeter is capable of obtaining an appropriate photoelectric pulse wave signal having a sufficiently large magnitude and thereby providing blood oxygen saturation readings in a reliable and precise manner.

In a preferred embodiment of the pulse oxymeter of the present invention, the warming means comprises a heat conductor body which is adapted to contact the body portion of the subject, and a heater for generating heat, the heat conductor body conducting the heat generated by the heater, to the body portion of the subject, so as to warm the body portion, the heat conductor body and the heater being supported by the probe.

In an advantageous form of the above-indicated embodiment of the invention, the warming means further comprises a thermometer for measuring a temperature of the heat conductor body, and a control means for controlling the heat generation of the heater based on the measured temperature of the heat conductor body.

In the above-indicated form, the warming means may further comprise a deep body thermometer for measuring a deep body temperature of the subject, the control means controlling the heat generation of the heater so that the measured temperature of the heat conductor body is equal to the measured deep body temperature. Alternatively, the warming means may further comprise an input means for specifying a reference temperature, the control means controlling the heat generation of the heater so that the measured temperature of the heat conductor body is equal to the reference temperature. In this case the reference temperature may be a normal deep body temperature.

In the same form of the pulse oxymeter of the invention, the heater may comprise a Peltier's element, the control means controlling the heat generation of the Peltier's element by changing directions of a direct electric current supplied to the Peltier's element. Alternatively, the heater may comprise a heating wire surrounding the first and second devices supported by the probe, the control means controlling the heat generation of the heating wire by adjusting electricity supplied to the heating wire.

In another embodiment of the pulse oxymeter of the invention, the warming means generates heat when the magnitude of the photoelectric pulse wave signal is below a reference level.

In yet another embodiment of the pulse oxymeter of the invention, the first device comprises a plurality of first light emitting elements and the second device comprises a plurality of second light emitting elements, the first and second light emitting elements being alternately disposed along a circle, the second device being disposed at a center of the circle.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which:

FIG. 3 is a flow chart according to which the pulse oxymeter of FIG. 1 is operated to measure a blood oxygen saturation;

FIG. 5 is a view of another embodiment of the present invention; and

FIG. 6 is a view of a portion of the embodiment of FIG. 5.

DETAILED DESCRIPTION OF THE PREFERRED EMBODIMENTS

Figure 1:
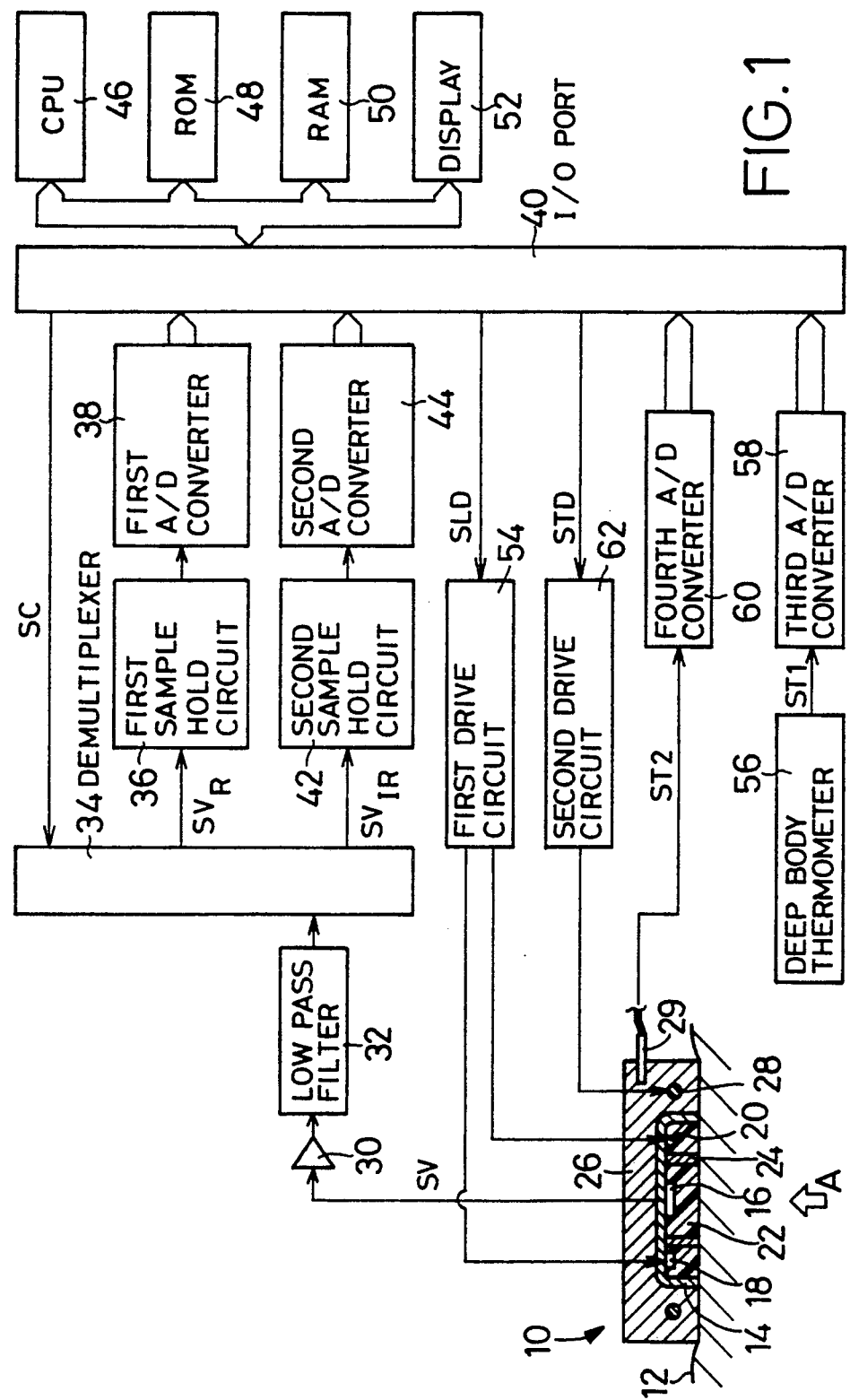
FIG. 1 is a diagrammatic view of a pulse oxymeter having a probe, which embodies the present invention.

Referring first to FIG. 1 there is shown a pulse oxymeter embodying the present invention. In the figure reference numeral 10 designates a probe which is adapted to be set on a body surface 12 of a subject with the help of a band (not shown) such that the probe 10 closely contacts the body surface 12 with a suitable pressing force. The body surface 12 may be the surface of a finger where the density of peripheral blood vessels including capillaries is comparatively high.

Figure 2:
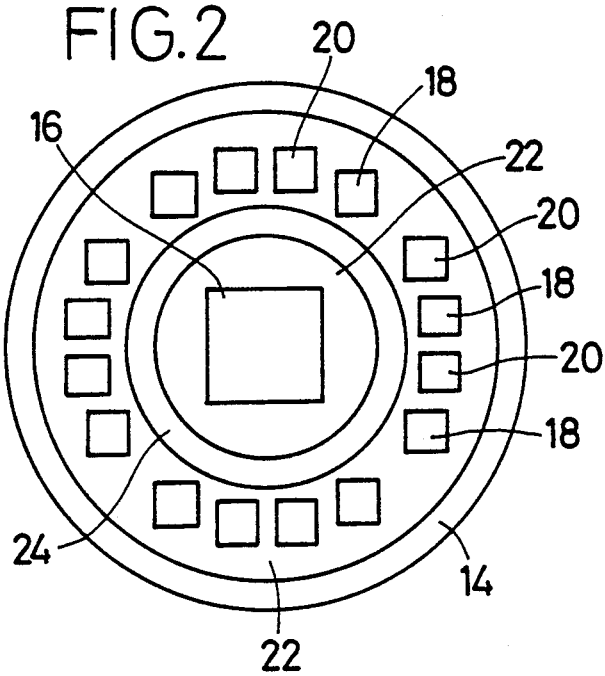
FIG. 2 is an enlarged view of the probe of FIG. 1 as viewed in a direction indicated at A in FIG. 1, with a heat conductor body thereof removed.

The probe 10 includes a cylindrical support member 14, a light detector 16, a first group of light emitting elements 18, a second group of light emitting elements 20, a transparent resin body 22, a cylindrical light shading member 24, a cylindrical heat conductor body 26, and an annular electric heater 28. The cylindrical support 14 has a comparatively shallow bottom, and supports at the center of an inside bottom surface thereof the light detector 16. The light detector 16 is constituted by a photodiode or a phototransistor, for example. As clearly shown in FIG. 2, the first and second groups of light emitting elements 18, 20 are supported on the inside bottom surface of the support 14 such that the eight first light emitting elements 18 and the eight second light emitting elements 20 are alternately disposed around the light detector 16 along a circle whose center coincides with the center of the inside bottom surface of the support 14. Each of the first and second light emitting elements 18, 20 is constituted by an LED (light emitting diode), for example. The transparent resin body 22 fills the shallow space inside the support 14 and covers the light detector 16 and the light emitting elements 18, 20. The cylindrical light shading member 24 is disposed between the light detector 16 and the light emitting elements 18, 20 in the shallow space inside the support 14, so that the shading member 24 prevents the lights emitted by the light emitting elements 18, 20 and reflected by the body surface 12, from being detected by the light detector 16. The cylindrical heat conductor body 26 is adapted to receive therein the cylindrical support 14, such that the heat conductor body 26 covers an outside bottom surface and an outside circumferential surface of the support 14. The heat conductor body 26 is formed of aluminum, for example. The annular electric heater 28 is constituted by a metallic wire, for example, and is embedded in the heat conductor body 26 so as to surround the cylindrical support 14. A thermometer 29 is inserted at the tip thereof in a hole formed in an outside circumferential surface of the heat conductor body 26. The thermometer 29 is constituted by a thermistor, for example.

With the pulse oxymeter probe 10 set on the body surface 12 of the subject, the heat conductor body 26 closely contacts the body surface 12, so that the electric heater 28 and the heat conductor body 26 cooperate with each other to heat or warm the underlying blood vessels bed containing the peripheral blood vessels including capillaries. In the present invention, the electric heater 28, the heat conductor body 26 and others cooperate with each other to serve as warming means for warming a body portion of a subject where a blood oxygen saturation is measured.

The eight first light emitting elements 18 are adapted to emit a red light having a wavelength of about 660 m$\mu$, and the eight second light emitting elements 20 are adapted to emit an infrared light having a wavelength of about 800 m$\mu$. Various pairs of lights each pair of which have different wavelengths may be employed in place of the 660 m$\mu$ and 800 m$\mu$ wavelengths lights, so long as one light of each pair exhibits significantly different absorption factors with respect to hemoglobin and oxygenated hemoglobin, respectively, and the other light exhibits generally same absorption factors with respect to the two sorts of hemoglobin, respectively. The first group of light emitting elements 18 and the second group of light emitting elements 20 alternately and periodically emit red and infrared lights, respectively, such that a one-time light emission from each group continues a predetermined, very short duration of time. The red and infrared lights emitted by the first and second groups of light emitting elements 18, 20, are reflected from the blood vessels bed under the body surface 12, and the reflected lights are detected by the common light detector 16.

The light detector 16 generates an electric signal SV whose magnitude corresponds to the detected intensity of a reflected red or infrared light, to a low pass filter 32 via an amplifier 30. The magnitude of the electric signal SV is variable because of the pulsation of arterial vessels in the blood vessels bed under the body surface 12. In the present embodiment, the electric signal SV serves as a photoelectric pulse wave signal. The low pass filter 32 clears the electric signal SV of noise whose frequencies are higher than a frequency of the arterial pulsation, and supplies the cleared electric signal SV to a demultiplexer 34. The demultiplexer 34 is selectively placed in a first and a second position thereof according to a switch signal SC (described below), in synchronization with the alternate and periodic light emissions from the first and second groups of light emitting elements 18, 20. More specifically, when the first group of light emitting elements 18 emit a red light, the demultiplexer 34 is placed in the first position in which the demultiplexer 34 permits an electric signal $SV_R$ representative of the detected intensity of the reflected red light, to be supplied to an I/O (input & output) port 40 via a first sample hold circuit 36 and a first A/D (analog to digital) converter 38. Meanwhile, when the second group of light emitting elements 20 emit an infrared light, the demultiplexer 34 is placed in the second position in which the demultiplexer 34 permits an electric signal $SV_{IR}$ representative of the detected intensity of the reflected infrared light, to be supplied to the I/O port 40 via a second sample hold circuit 42 and a second A/D converter 44. Thus, when the first and second groups of light emitting elements 18, 20 alternately and periodically emit red and infrared lights, respectively, the demultiplexer 34 is correspondingly switched between the first and second positions. The first and second sample hold circuits 36, 42 supply the electric signals $SV_R$, $SV_{IR}$ to the first and second A/D converters 38, 44, respectively, such that the circuits 36, 42 continue to hold the signals $SV_R$, $SV_{IR}$ received in a current cycle until the converters 38, 44 have completed the analog to digital conversions of the signals $SV_R$, $SV_{IR}$ which in the preceding cycle the circuits 36, 42 have supplied to the converters 38, 44, respectively.

The I/O port 40 is connected via data bus to a CPU (central processing unit) 46, a ROM (read only memory) 48, a RAM (random access memory) 50, and a display 52. The CPU 46 operates for determining a blood oxygen saturation of the subject, by utilizing the temporary storage function of the RAM 50 according to programs pre-stored in the ROM 48. More specifically, the CPU 46 generates a light emit signal SLD to a first drive circuit 54 via the I/O port 40 so that the first and second groups of light emitting elements 18, 20 alternately and periodically emit red and infrared lights having the different wavelengths, respectively. In synchronization with the alternate and periodic red and infrared lights emissions from the first and second groups of light emitting elements 18, 20, the CPU 46 generates the switch signal SC to the demultiplexer 34 via the I/O port 40 so as to correspondingly place the demultiplexer 34 in the first or second position. Thus, the signal components $SV_R$, $SV_{IR}$ included in the signal SV are separated from each other by the demultiplexer 34 such that the signal $SV_R$ is supplied to the first sample hold circuit 36 while the signal $SV_{IR}$ is supplied to the second sample hold circuit 42. Further, the CPU 46 processes the signals supplied from the first and second A/D converters 38, 44, according to programs pre-stored in the ROM 48, and thereby determines an oxygen saturation of the blood flowing through the peripheral blood vessels under the body surface 12. The CPU 46 commands the display 52 to indicate the determined blood oxygen saturation.

A deep body thermometer 56, which is well known in the art, is set in the neighborhood of the probe 10 on the body surface 12. The thermometer 56 supplies a first temperature signal ST1 representative of a temperature of a deep body portion of the subject, to the CPU 46 via a third A/D converter 58. In addition, the CPU 46 receives from the thermometer 29 via a fourth A/D converter 60 a second temperature signal ST2 representative of a temperature of the heat conductor body 26. The CPU 46 processes the first and second temperature signals ST1, ST2 supplied from the thermometers 29, 56 according to programs pre-stored in the ROM 48, and generates a drive signal STD to a second drive circuit 62 so as to control the heat generation of the electric heater 28 so that the temperature of the heat conductor body 26 becomes equal to the deep body temperature of the subject. The second drive circuit 62 adjusts electricity supplied to the electric heater 28 according to the drive signal STD.

There will be described the operation of the present pulse oxymeter for measuring a blood oxygen saturation of the subject, which operation is carried out according to the flow chart of FIG. 3.

The control of the CPU 46 begins with Step S1 of the flow chart of FIG. 3, in which step the first group of light emitting elements 18 and the second group of light emitting elements 20 alternately emit the red and infrared lights, periodically at an appropriate frequency. This frequency is so determined that the present pulse oxymeter obtains a satisfactory photoelectric pulse wave signal having a sufficiently high density of data points each of which corresponds to an electric signal $SV_R$ or $SV_{IR}$. More specifically, each time the first group of light emitting elements 18 emit a red light, the present pulse oxymeter obtains a signal $SV_R$ representative of the detected intensity of the red light reflected from the blood vessels bed. Similarly, each time the second group of light emitting elements 20 emit an infrared light, the pulse oxymeter obtains a signal $SV_{IR}$ representative of the detected intensity of the infrared light reflected from the blood vessels bed. As previously described, the magnitude of the photoelectric pulse wave signal varies in synchronization with the pulsation of the arterial vessels of the subject.

Figure 4:
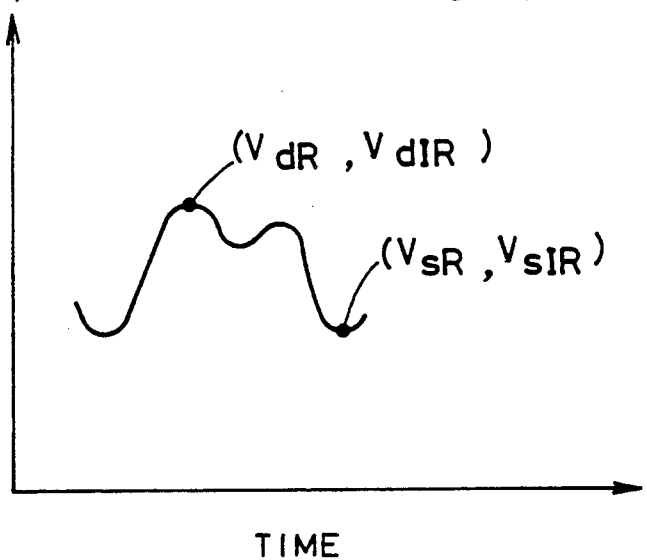
FIG. 4 is a view of a graph indicating the intensities of a reflected light detected by a light detector of the pulse oxymeter of FIG. 1.

Step S1 is followed by Step S2 in which it is judged whether or not a photoelectric pulse wave signal corresponding to a one-time pulsation of the arterial vessels, namely one pulse of the pulse wave signal, has been obtained. In other words, it is judged whether or not the data points or signals $SV_R$, $SV_{IR}$ sufficient to provide one pulse of the pulse wave signal, have been collected. In the event that the judgement in Step S1 is negative, the control of the CPU 46 remains in Step S2 and waits. Meanwhile, if the judgement in Step S2 is turned affirmative, the control of the CPU 46 proceeds with Step S3 in which the CPU 46 determines an upper peak value $V_{dR}$ and a lower peak value $V_{sR}$ of the above-indicated one pulse corresponding to the red light, and an upper peak value $V_{dIR}$ and a lower peak value $V_{sIR}$ of the above-indicated one pulse corresponding to the infrared light. The values $V_{dR}$ and $V_{dIR}$ are representative of the corresponding intensities of the red and infrared lights reflected from the body when the heart of the subject dilates in a diastolic period. Meanwhile, the values $V_{sR}$ and $V_{sIR}$ are representative of the corresponding intensities of the reflected red and infrared lights when the heart of the subject constricts in a systolic period. In FIG. 4 there is shown a graph indicating a single waveform of a photoelectric pulse wave signal representative of the time-wise variation in intensity of the reflected red or infrared light. The amplitude of the pulse wave signal reflects a fraction of the red or infrared light which is absorbed by the arterial vessels (or arterial blood flowing therethrough), and an oxygen saturation of the arterial blood.

Step S3 is followed by Step S4 in which the CPU 46 calculates values $(V_{dR}-V_{sR})$, $(V_{dR}+V_{sR})$, $(V_{dIR}-V_{sIR})$, and $+V_{sIR})$ based on the upper and lower peak values determined in Step S3, and further calculates the following ratios A and B. Utilization of the ratios A, B ensures that the oxygen saturation readings are free from various influences such as the used intensities of the light emitting elements 18, 20, the specific properties of the light detector 16, the light absorbing characteristics of the skin pigmentation or color of the subject, and the light diffusing and absorbing characteristics of the blood vessel bed (these characteristics may vary depending upon wavelengths of the used lights). Step S4 is followed by Step S5 in which the following value A/B is calculated.

$$A = (V_{dR} - V_{sR})/(V_{dR} + V_{sR})$$

$$B = (V_{dIR} - V_{sIR})/(V_{dIR} + V_{sIR})$$

$$A/B = \frac{(V_{dR} - V_{sR})/(V_{dR} + V_{sR})}{(V_{dIR} - V_{sIR})/(V_{dIR} + V_{sIR})}$$

Step S5 is followed by Step S6 in which the CPU 46 determines an actual blood oxygen saturation based on the value A/B obtained in Step S5, according to a predetermined relationship between value A/B and blood oxygen saturation. Subsequently the control of the CPU 46 proceeds with Step S7 in which the CPU 46 commands the display 52 to indicate the determined blood oxygen saturation value. Thereafter the control of the CPU 46 goes back to Step S2 and then the following steps. Thus, each time a one-pulse photoelectric signal is obtained, the pulse oxymeter determines a blood oxygen saturation value and indicates the value on the display 52, whereby the blood oxygen saturation values are continuously indicated.

For blood oxygen saturation measurement it is required that a sufficient amount of pulsating current flow through capillaries in the underlying blood vessel bed. In the event that the blood oxygen saturation is monitored on a patient who is undergoing a surgical operation, the peripheral blood vessels of the patient may constrict because of invasion or stress due to use of a surgical knife or administration of a drug and consequently the blood flow through the peripheral blood vessels may be reduced to an insufficient amount, or completely lost. In such events, an appropriate photoelectric pulse wave signal having a sufficient magnitude is not obtained, and the blood oxygen saturation is not monitored in a reliable and precise manner, or the monitoring itself fails.

In the present embodiment, however, the blood vessel bed under the body surface 12 from which the blood oxygen saturation readings are obtained, is warmed to, and maintained at, a temperature equal to a deep body temperature of the patient by the electric heater 29 and the heat conductor body 26 supported by the probe 10. Thus, the present pulse oxymeter advantageously prevents the constriction of the peripheral blood vessels in the above-indicated events and thereby ensures that a sufficient amount of blood flows through the peripheral blood vessels and capillaries. In other words, the present pulse oxymeter is capable of obtaining an appropriate photoelectric pulse wave signal (electric signal SV) having a satisfactory magnitude, even in the above-indicated events. Thus, the pulse oxymeter is capable of measuring a blood oxygen saturation in a more reliable and precise manner than the conventional pulse oxymeters. In addition, the present pulse oxymeter ensures that a blood oxygen saturation is measured with respect to a body portion where the density of peripheral blood vessels is comparatively low.

In the illustrated embodiment, the plurality of first light emitting elements 18 and the plurality of second light emitting elements 20 are alternately disposed along the same circle whose center is located at the position where the light detector 16 is disposed. Thus, the intensity of a red or infrared light reflected from the body is increased, and therefore the reflected light is advantageously detected by the light detector 16. In addition, in the event that the endothelium and/or subcutaneus tissues of the blood vessel bed have an ill-balanced structure, for example in the event that a relatively large vein extends through the blood vessel bed, the adverse influence of the ill-balanced structure to the detection of the reflected red or infrared light, is minimized by averaging of the reflected light due to the above-indicated construction of the first and second light emitting elements 18, 20 and light detector 16. Furthermore, in the event that the position of the probe 10 becomes inclined with respect to the body surface 12 and consequently a spacing is produced therebetween, the adverse influence of the spacing to the detection of the reflected red or infrared light is also minimized.

Referring next to FIGS. 5 and 6 there will be described a second embodiment of the pulse oxymeter of the present invention. In the following description, the same reference numerals as used in the description of the preceding embodiment are used to designate the corresponding elements or parts of the second embodiment and the description of those elements or parts is skipped.

In the instant embodiment, a Peltier's element 70 is disposed on an upper surface of a heat conductor body 26 serving as a main body of a probe 10. On an upper surface of the Peltier's element 70 is disposed a fin 72 serving for radiating heat. As shown in FIG. 6 the Peltier's element 70 includes two sorts of metallic blocks 74 and 76 which are disposed in an alternate fashion and connected to each other at first connection areas 78 on the side of the heat conductor body 26 and at second connection areas 80 on the side of the radiator fin 72. When a drive device 82 supplies in a normal manner an electric current to the Peltier's element 70, the first connection areas 78 generate heat while the second connection areas 80 sink or absorb heat. The two sorts of metallic bodies 74, 76 are formed of bismuth and antimony, respectively, or of copper and iron, respectively. Reference numerals 84 and 86 designate insulator layers formed of an electrically insulating material having a high heat conductivity, such as ceramics, or resin films containing metallic particles.

In the instant embodiment a temperature controller 90 supplies a control signal to the drive device 82 so that the temperature detected through a thermistor 29 is equal to a reference temperature pre-set through an input device 88. The drive device 82 supplies the Peltier's element 70 with a direct current according to the control signal supplied from the controller 90. More specifically, if the temperature detected through the thermistor 29 exceeds the reference temperature the controller 90 controls the drive device 82 to change directions of the direct current supplied to the Peltier's element 70, so that the first and second connection areas 78, 80 operate in the reverse manner, namely, the first connection areas 78 sink heat while the second connection areas 80 generate heat. In the event that the temperature detected through the thermistor 29 is lowered to below the reference value the controller 90 controls the drive device 82 to re-change the directions of the direct current supplied to the Peltier's element 70, so that the first connection areas 78 generate heat while the second connection areas 80 sink heat. Thus, the temperature of the heat conductor body 26 is advantageously maintained at a temperature equal to the reference value. The reference value may be selected at a normal or mean deep body temperature of human beings, or may be selected at an appropriate value irrespective of deep body temperature. In the instant embodiment the Peltier's element 70, the drive device 82, the temperature controller 90, and the input device 88 cooperate with each other to serve as the warming means. In place of the input device 88, it is possible to employ a deep body thermometer 56 as previously described. In this case, the controller 90 controls the drive device 82 so that the temperature of the heat conductor body 26 (or probe 10) is equal to the deep body temperature detected by the thermometer 56.

While the present invention has been described in its presently preferred embodiments, it is to be understood that the present invention is not limited to the details of the illustrated embodiments but may be otherwise embodied.

For example, while in the illustrated embodiments the heating wire 28 and the Peltier's element 70 are used for warming a body portion of the subject, it is possible to employ in place thereof a light emitting device such as an LED as the warming means.

In addition, according to the principle of the present invention, the warming means may be adapted to warm a body portion of the subject only when the magnitude of a photoelectric pulse wave signal detected by the pulse oxymeter is below a predetermined value. In this case the warming means serves for expanding or dilating the constricted peripheral blood vessels and capillaries.

The first and second groups of light emitting elements 18, 20 used in the illustrated embodiments may be replaced by a single first and a single second light emitting element.

While the illustrated pulse oxymeters each are of the reflection type, the present invention may be applied to a pulse oxymeter of the transmission type which is adapted to utilize the lights transmitted through a body portion of a subject. Moreover, the present invention is applicable to a pulse oxymeter of the type which is adapted to utilize three or more sorts of lights having different wavelengths for measuring a blood oxygen saturation.

It is to be understood that the present invention may be embodied with other changes, modifications and improvements that may occur to those skilled in the art without departing from the scope and spirit of the invention as defined in the appended claims.

What is claimed is:

1. A pulse oxymeter for measuring a blood oxygen saturation of a subject, including (a) a first device for emitting toward a body portion of the subject a first light having a first wavelength and a second light having a second wavelength different from the first wavelength, (b) a second device for detecting an intensity of each of the first and second light transmitted through, or reflected by, the body portion of the subject and generating a photoelectric pulse wave signal representative of the detected intensity of each of the first and second lights, (c) a third device for determining a blood oxygen saturation of the subject based on the pulse wave signals corresponding to the first and second lights, (d) a heat conductor body adapted to contact the body portion, (e) a temperature changing device for changing a temperature of the heat conductor body, (f) a measuring device for measuring the temperature of the heat conductor body, and (g) a probe which supports the first and second devices, heat conductor body, and temperature changing device, wherein the improvement comprises:

a deep body thermometer for measuring a deep body temperature of said subject; and
control means for controlling said temperature changing device so that the measured temperature of said heat conductor body is equal to the measured deep body temperature of said subject.

2. The pule oxymeter as set forth in claim 1, wherein said temperature changing device comprises a Peltier's element, said control means controlling said Peltier's element by changing directions of a direct electric current supplied to said Peltier's element.

3. The pulse oxymeter as set forth in claim 1, wherein said temperature changing device comprises a heating wire, said control means controlling the heat generation of said heating wire by adjusting electrical power supplied to said heating wire.

4. The pulse oxymeter as set forth in claim 1, wherein said first device comprises a plurality of first light emitting elements and a plurality of second light emitting elements, said first and second light emitting elements being alternately disposed along a circle, said second device being disposed at a center of said circle.

5. A pulse oxymeter for measuring a blood oxygen saturation of a subject, including (a) a first device for emitting toward a body portion of the subject a first light having a first wavelength and a second light having a second wavelength different from the first wavelength, (b) a second device for detecting an intensity of each of the first and second lights transmitted through, or reflected by, the body portion of the subject and generating a photoelectric pulse wave signal representative of the detected intensity of each of the first and second lights, (c) a third device for determining a blood oxygen saturation of the subject based on the pulse wave signals corresponding to the first and second lights, (d) a heat conductor body adapted to contact the body portion, (e) a temperature changing device for changing a temperature of the heat conductor body, and (f) a supporting device for supporting the first device, second device, heat conductor body, and temperature changing device, wherein the improvement comprises:

said temperature changing device comprising a Peltier's element, said Peltier's element contacting said heat conductor body;
said temperature changing device further comprising heat radiating means for radiating heat, said heat radiating means having a first surface contacting said Peltier's element and a second surface contacting ambient atmosphere; and
control means for controlling said Peltier's element by changing directions of a direct electric current supplied to the Peltier's element, so that the Peltier's element generates heat to said heat conductor body, or sinks heat from the heat conductor body.

6. The pulse oxymeter as set forth in claim 5, further comprising:

measuring means for measuring the temperature of said heat conductor body; and
input means for specifying a reference temperature;
said control means controlling said Peltier's element so that the measured temperature of said heat conductor body is equal to said reference temperature.

7. The pulse oxymeter as set forth in claim 6, wherein said reference temperature is a normal deep body temperature.

8. The pulse oxymeter as set forth in claim 5, further comprising:

first measuring means for measuring the temperature of said heat conductor body; and second measuring means for measuring a deep body temperature of said subject;

said control means controlling said Peltier's element so that the measured temperature of said heat conductor means is equal to the measured deep body temperature of said subject.

9. The pulse oxymeter as set forth in claim 5, wherein said control means controls said Peltier's element so that the Peltier's element generates heat when the magnitude of said photoelectric pulse wave signal is below a reference level.

10. The pulse oxymeter as set forth in claim 5, wherein said first device comprises a plurality of first light emitting elements and a plurality of second light emitting elements, said first and second light emitting elements being alternatively disposed along a circle, said second device being disposed at a center of said circle.

11. The pulse oxymeter as set forth in claim 5, wherein said heat radiating means comprises a fin.

* * * * *